United States Patent [19]

Voss et al.

[11] Patent Number: 5,770,781
[45] Date of Patent: Jun. 23, 1998

[54] METHOD FOR ELIMINATING CARBON OXIDES IN FEEDS TO A C5 AND C6 PARAFFIN ISOMERIZATION PROCESS

[75] Inventors: Andrew P. Voss, Cerritos; Michael J. Pedersen, Irvine, both of Calif.

[73] Assignee: Atlantic Richfield Company, Los Angeles, Calif.

[21] Appl. No.: 732,823

[22] Filed: Oct. 15, 1996

[51] Int. Cl.$^6$ .............................. C07C 5/22; C07C 1/00; C07C 5/13

[52] U.S. Cl. ........................ 585/253; 585/266; 585/304; 585/317; 585/734; 423/658.3

[58] Field of Search .................................... 585/253, 266, 585/304, 317, 734; 423/658.3

[56] References Cited

PUBLICATIONS

R. Kramer, M. Fishbacher and H. L. Gruber, "Slow Uptake of Oxygen and Carbon Monoxide bghy Platinum/Silica (Europt–1) and Subsequent Effects on Hydrogenation of Benzene and Hydrogenolysis of Methycyclopentane", *Applied Catalysis*, 42 (1988) 337–350, Elsevier Science Publishers B.V., Amsterdam—Printed in The Netherlands.

Geltramini, "Catalytic Naphtha Reforming", edited by G.J. Antos, et al; 1995, Mar., Dekket, Inc., pp. 314–315.

Rylander, Paul Nels, Catalytic Hydrogenation over Platinum Metals, New York, Academic Press, 1967, p. 20.

"IFP Process Literature" (Sales Material generally available to Refiners).

"Setting the Pace with IFP for the 21st Century", Jun. 1994 (Promotional Literature from IFP that is generally available to refiners).

Schmidt, R.J., Weiszmann, J.A., and Johnson, J.A., "Catalysts—key to low–cost isomerization", Oil & Gas Journal, May 27, 1985, pp. 80–88.

Schmidt, R.J., Johnson, J.A., Hibbs, F.M. and Froggatt, M.D., "Two New Catalysts for Isomerization of Light Straight Run Naphtha", For Presentation at the Fourth Scientific Conference, Scientific Research Council, Baghdad, Iraq, Oct. 23–28, 1986.

Johnson, J.A., Hobbs, S.H., Wheeler, T., "UOP PENEX Technology—A Flexibile Solution", May 5, 1986.

"Section 11 Isomeriztion", *Modern Refinery Operations & Practices*, Hydrocarbon Publishing Co., 1993, pp. 94–97.

Symoniak, M.F. and Holcombe, T.C., "Total Isomerization Gains Flexibility", *Hydrocarbon Processing*, May 1983, pp. 62–64.

(List continued on next page.)

*Primary Examiner*—Glenn Caldarola
*Assistant Examiner*—In Suk Bullock
*Attorney, Agent, or Firm*—F. Lindsey Scott

[57] ABSTRACT

A method for reducing the benzene content and isomerizing at least a portion of a $C_5/C_6$ paraffinic stream using a hydrogen stream containing more than 0.1 ppmv of carbon monoxide, carbon dioxide or a mixture thereof, the method comprising: charging a $C_5/C_6$ paraffin stream containing benzene to a benzene saturation zone; charging a hydrogen stream containing at least 0.1 ppmv of at least one carbon oxide to the benzene saturation zone; saturating at least a major portion of the benzene and methanating at least a major portion of the carbon oxide present in the benzene saturation zone to produce a reduced benzene content $C_5$ and $C_6$ paraffinic stream and a reduced carbon oxide content hydrogen stream; recovering the reduced benzene content $C_5$ and $C_6$ paraffinic stream and the reduced carbon oxide content hydrogen stream; drying at least a portion of the reduced carbon oxide content hydrogen stream to produce a dried reduced carbon oxide content hydrogen stream; charging at least a portion of the dried reduced carbon oxide content hydrogen stream to a $C_5/C_6$ isomerization zone; charging at least a portion of the reduced benzene content $C_5/C_6$ paraffinic stream to the $C_5/C_6$ isomerization zone; and, isomerizing at least a portion of the reduced benzene content $C_5/C_6$ paraffinic stream in the $C_5/C_6$ isomerization zone to produce an isomerized $C_5/C_6$ paraffin stream.

13 Claims, 3 Drawing Sheets

OTHER PUBLICATIONS

"Isomerization", *Hydrocarbon Processing,* Nov. 1990, p. 122.

*Chemical and Process Technology Encyclopedia,* Douglas M. Considine, Editor, McGraw–Hill Book Co., 1974, pp. 662–665.

Schmidt, R.J. and Weiszmann, J.A., "Low Cost Options for Upgrading Light Straight Run Naphtha", American Petroleum Institute, 1985, 30 pp.

"Applications for Isomerization Processes", ICI PURASPEC Processes, ICI Katalco, Two TransAm Plaza Drive, Oakbrook Terrace, Illinois 60181, 1993, 6 pp.

Lietz, G., and Volter, J., Catalytic Hydrogenation of Methylbenzenes on Platium, Symposium on the Mechanisms of Hydrocarbon Reactions 5–7 Jun., 1973 Siofok, Hungary, pp. 151–161.

Hibbs, F.M., "New Technologies for Efficient Refining inthe Environmentally Conscious 1990s", Petroleum Review, May 1994, pp. 210–213.

U.S. Patent Application, Voss, Andrew P. et al, "A Method for Eliminating Carbon Oxides in the Hydrogen Feed to a Butane Isomerization Process", filed Oct. 16, 1996. (Serial No. 08/732,828).

METHOD FOR ELIMINATING CARBON OXIDES IN FEEDS TO A C5 AND C6 PARAFFIN ISOMERIZATION PROCESS

BACKGROUND OF THE INVENTION

1. Field of the Invention

This invention relates to a method for reducing the benzene content and isomerizing a predominantly $C_5$ and $C_6$ paraffin stream using a hydrogen stream containing at least one carbon oxide.

2. Description of Related Art

In refinery processes it is desirable that a substantial portion of the crude oil or other petroleum feed stock to the refinery be converted to gasoline range materials. Gasoline comprises a hydrocarbon fraction generally having a boiling range of about 30° to about 430° F. and a research octane number (RON) of at least about 90. A variety of refinery processes are used to increase the gasoline yield from crude oil charged to a refinery. Such processes include catalytic cracking, reforming, alkylation and the like. In the refining process naphthenic and paraffinic hydrocarbons are produced which are of a suitable boiling range for use as gasoline but which have an octane rating too low for use as gasoline. The octane rating of such hydrocarbons is typically increased by reforming. In the reforming process, the naphthene hydrocarbons and paraffin hydrocarbons are converted to aromatic hydrocarbons. As is well known to those skilled in the art, aromatic materials have a higher octane rating than similar boiling range paraffinic or naphthenic materials.

While such reforming processes are effective to produce higher octane rating materials, the materials so produced are aromatic and in recent years there have been requirements to reduce the aromatic component content of gasoline. While reforming remains a valuable tool for increasing the octane rating of paraffinic hydrocarbons increased attention has been directed to other methods for increasing the octane rating of paraffinic hydrocarbons.

One such method is the use of isomerization. Isomerization of gasoline range paraffins is frequently used with paraffinic hydrocarbons which comprise primarily paraffinic hydrocarbons containing from 5 to 6 carbon atoms. Such $C_5/C_6$ streams are frequently subjected to benzene saturation and isomerization treatment to saturate benzene and convert straight chain hydrocarbons to branched chain, or isomerized, $C_5$ and $C_6$ paraffins which have a higher octane rating than the corresponding straight chain paraffins.

Such isomerization processes are well known to those skilled in the art as discussed in *Chemical and Process Technology Encyclopedia*, Douglas M. Considine, Ed., McGraw Hill Book Company, 1974, pp. 662–665. As discussed in this reference it is a common practice to also isomerize $C_4$ hydrocarbons for use in alkylation processes and the like. It is also noted that moisture must be minimized in the isomerization zone and that the amount of benzene in the paraffin feed stock should be minimized. It is also known to those skilled in the art that carbon oxides, even in small amounts, in the feed stream are extremely detrimental to the isomerization catalyst. Such carbon oxides are methanated over the isomerization catalyst. The methanation reaction produces water which permanently poisons the isomerization catalyst. Accordingly it has long been recognized that carbon oxides in the feed to the isomerization reactor must be minimized and desirably maintained at levels below 0.1 part per million by volume (ppmv).

It has also been recognized that the presence of benzene in the paraffin feed to the isomerization reactor is detrimental since the benzene is hydrogenated over the isomerization catalyst causing an increase in reactor temperature which promotes unwanted cracking reactions and increased hydrogen consumption. Thus it is desirable to remove benzene before the isomerization reaction zone in a unit such as a benzene hydrogenation reactor.

Benzene saturation units have long been known to those skilled in the art and are used to saturate benzene compounds in paraffinic streams. Such processes typically use a catalyst comprising from about 0.1 to about 1.0 weight percent platinum on a suitable catalyst support such as alumina or silica alumina. Such units typically operate at an inlet temperature from about 325° to 800° F. and a pressure from about 200 to 700 pounds per square inch gauge (psig). Since carbon oxides temporarily poison the catalyst in the benzene saturation reactor it has been considered necessary to maintain the carbon oxide content of the streams charged to the benzene saturation reactor at low levels.

In recent years there has been increased interest in removing benzene components from $C_5/C_6$ paraffinic streams and isomerizing $C_5/C_6$ paraffinic streams because of the increased emphasis on the production of gasoline having a reduced aromatics content. Accordingly, improved methods have been sought for producing such gasolines from existing refinery streams.

In many refineries the available hydrogen sources contain amounts of carbon monoxide, carbon dioxide or mixtures thereof up to as much as about 100 ppmv. Accordingly, in the past such hydrogen streams have been passed through a methanation reactor to react the carbon oxides to produce water and methane with the resulting water being removed prior to charging the hydrogen to isomerization reactors. Similarly, the carbon oxides have been removed prior to using such hydrogen streams in benzene saturation reactors.

Accordingly, an improved method is desired for reducing the capital cost of such processes and effectively using hydrogen streams containing carbon oxides in benzene saturation and isomerization processes.

SUMMARY OF THE INVENTION

The method of the present invention permits the use of hydrogen streams containing at least one carbon oxide selected from the group consisting of carbon monoxide and carbon dioxide in processes for reducing the benzene content and isomerizing at least a portion of a paraffinic stream containing at least 50 percent $C_5$ and $C_6$ paraffins and benzene, the method comprising:

a) charging a predominantly $C_5$ and $C_6$ paraffinic stream containing benzene to a benzene saturation zone;

a b) charging a hydrogen stream containing at least one carbon oxide to the benzene saturation zone;

c) saturating at least a major portion of the benzene and methanating at least a major portion of the carbon oxide present in the benzene saturation zone at a temperature from about 325° to about 800° F., and a pressure from about 200 to about 700 psig in the presence of a benzene saturation catalyst to produce a reduced benzene content paraffinic stream and a reduced carbon oxide content hydrogen stream;

d) recovering the reduced benzene content paraffinic stream and the reduced carbon oxide content hydrogen stream;

e) drying at least a portion of the reduced carbon oxide content hydrogen stream to produce a dried reduced carbon oxide content hydrogen stream;

f) charging at least a portion of the dried reduced carbon oxide content hydrogen stream to an isomerization zone;

g) charging at least a portion of the reduced benzene content paraffinic stream to the isomerization zone; and, h) isomerizing at least a portion of the reduced benzene content paraffinic stream in the isomerization zone at a temperature from about 250° to about 600° F, and a pressure from about 100 to about 600 psig in the presence of an isomerization catalyst to produce an isomerized paraffin stream.

DESCRIPTION OF THE PREFERRED EMBODIMENTS

In the description of the Figures the same numbers will be used throughout to refer to the same or similar components. Various pumps, valves and the like necessary to achieve the indicated flows have not been shown except when necessary for the process flow description.

Figure 1:
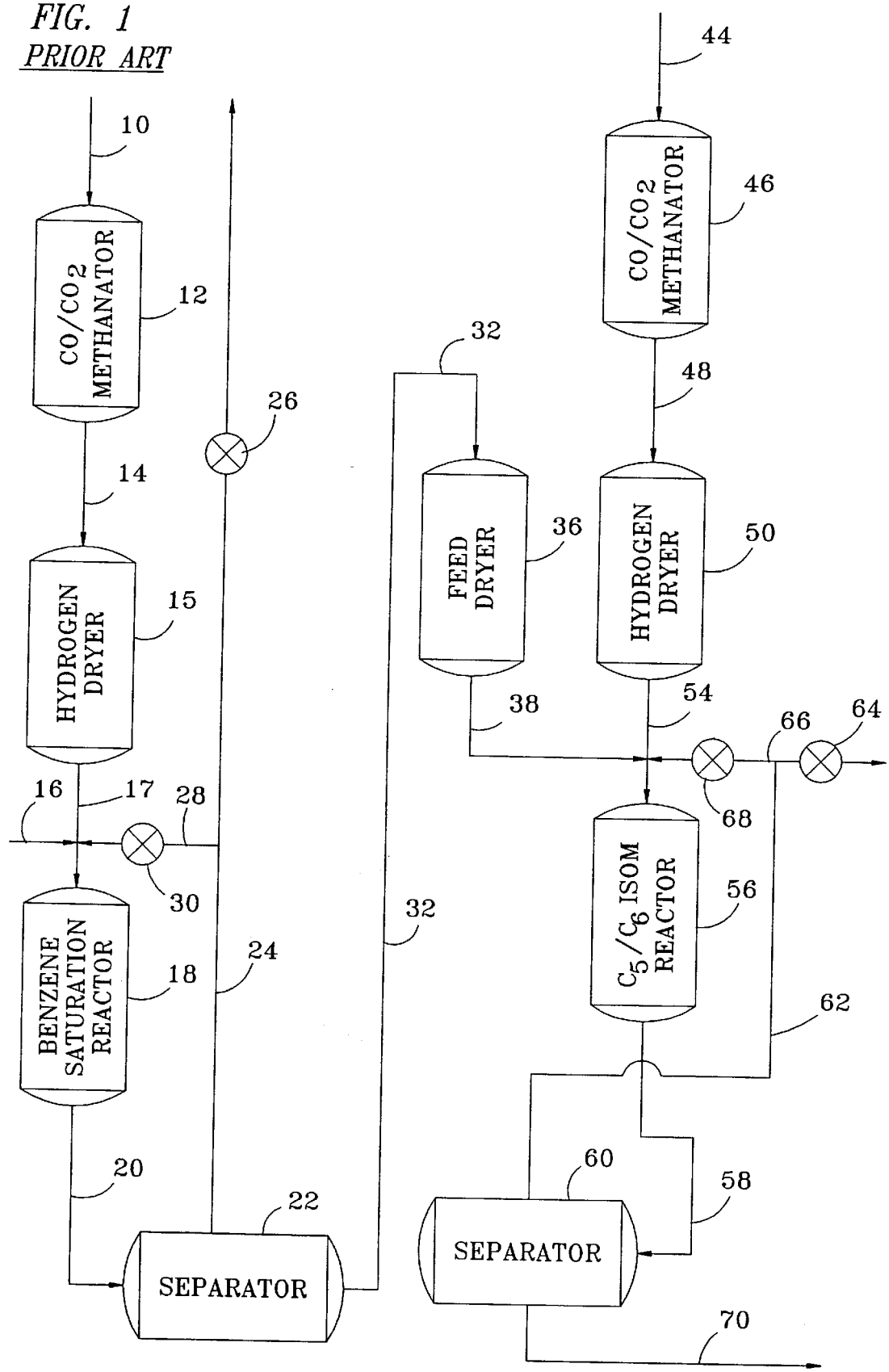
FIG. 1 is a schematic diagram of a prior art process wherein the benzene content of a predominantly $C_5$ and $C_6$ paraffin stream is reduced and wherein the reduced benzene content paraffin stream is isomerized to produce an isomerized paraffin stream.

In FIG. 1 a hydrogen line 10 supplies hydrogen containing more than 0.1 ppmv of at least one carbon oxide to a $CO/CO_2$ methanator 12 containing a suitable methanation catalyst which is typically a nickel-based catalyst. Methanation catalysts are considered to be well known to those skilled in the art as are methanation conditions. The resulting methanated stream containing hydrogen methane and water passes through a line 14 to a hydrogen dryer 15 where water is removed. Hydrogen dryer 15 may be any suitable hydrogen drying system. The dried hydrogen then passes through a line 17 to a benzene saturation reactor 18. A paraffinic feed stream containing at least 50 volume percent paraffins containing from 5 to 6 carbon atoms (herein $C_5$ and $C_6$ paraffins) and benzene is fed through a line 16 and combined with the hydrogen in line 17 for charging to benzene saturation reactor 18. The reaction product comprising the paraffinic stream having a reduced benzene content and hydrogen is recovered through a line 20 and passed to a separator 22 where the hydrogen is recovered through a line 24 and passed to discharge from the process through a valve 26 or recycled at least in part to benzene saturation reactor 18 through a line 28. The flows through lines 24 and 28 are controlled by a valve 30 in line 28 and valve 26 in line 24. While a portion of the hydrogen may be recycled to benzene saturation reactor 18 the hydrogen will contain methane from $CO/CO_2$ methanator 12 and other light gases. These gases must be periodically removed from the process when they reach unacceptable levels. The operation of such processes is considered to be well known to those skilled in the art.

The paraffinic product recovered from separator 22, is passed through a line 32 to a feed dryer 36. Feed dryer 36 may be any suitable hydrocarbon drying system. The dried paraffin stream is then recovered through a line 38 and passed through line 38 to combination with hydrogen in a line 54 and charged to an isomerization reactor 56.

Hydrogen for isomerization reactor 56 is supplied through a line 44 and as supplied includes more than 0.1 ppmv of at least one carbon oxide. The hydrogen is passed through line 44 to a $CO/CO_2$ methanator 46 where the carbon oxides are converted to methane and water. The resulting product stream is then passed through a line 48 to a hydrogen dryer 50 where water is removed by the use of any suitable hydrogen drying process. The dried hydrogen is passed through line 54 to isomerization reactor 56 in combination with the paraffinic feed stream from line 38.

The resulting reaction product comprising isomerized $C_5$ and $C_6$ paraffins and hydrogen is recovered through a line 58 and passed to a separator 60. In separator 60 the isomerized paraffin product is recovered through a line 70 and passed to use as a blending component of gasoline or the like. The recovered hydrogen, including methane and possibly other light hydrocarbons, is recovered through a line 62 and passed to discharge from the process via a valve 64 or alternatively recycled to isomerization reactor 56 via a line 66 and a valve 68.

The operation of benzene saturation processes and isomerization processes as described above is well known to those skilled in the art. In the benzene saturation reactor 18 a catalyst comprising from about 0.1 to about 1.0 weight percent platinum on alumina, aluminosilicate or the like may be used as a catalyst at a temperature typically from about 325° to about 800° F. and a pressure typically from about 200 to 700 psig. The paraffin stream space velocity in benzene saturation reactor 18 is typically from about 2 to about 10 liquid hourly space velocity (LHSV). Liquid Hourly Space Velocity is defined as the volume of liquid feed per unit volume of catalyst per hour. The operating temperature is limited by the upper operating temperature limits of the catalyst and reactor and may limit the amount of benzene which may be included in the charge to the reactor. The operating temperature is also limited by the chemical equilibrium of the benzene hydrogenation reaction which is not favorable above 800° F.

Suitable isomerization catalysts include supported platinum group metal catalysts which may comprise from about 0.1 to about 2.0 weight percent platinum group metal component supported on activated alumina, crystalline aluminosilicate or other suitable support materials. The catalyst may also contain rhodium group metal components as well as promoters. Such catalysts may contain up to 20 weight per cent acidic chloride components and are generally considered to be highly acidic catalysts. Such catalysts are considered to be known to the art.

The mixture of hydrogen and feed stock is typically charged to the isomerization reactor at a temperature from about 250° to about 600° F. and a pressure from about 100 to about 600 psig. The hydrogen is desirably supplied to such isomerization processes in an amount equal to about 500 to about 4,000 standard cubic feet per barrel of $C_5/C_6$ paraffin feed stock. The LHSV in isomerization reactor 56 is typically from about 1 to about 4.

Such process variations are considered to be well known to those skilled in the art.

Figure 2:
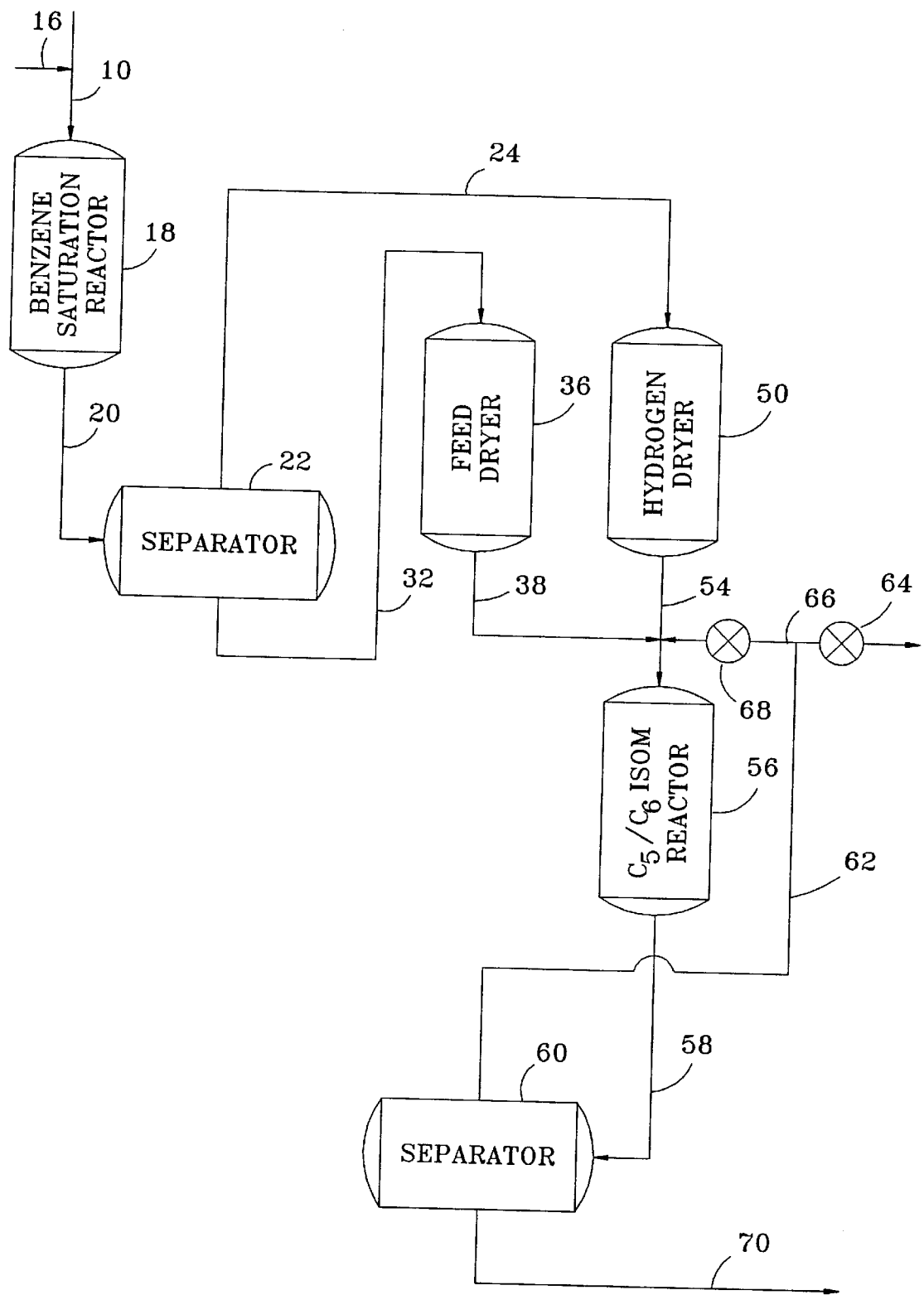
FIG. 2 is a schematic diagram of an embodiment of the present invention.

In FIG. 2 a process according to the present invention is shown. A hydrogen stream containing up to about 100 ppmv of carbon monoxide, carbon dioxide or mixtures thereof is charged to benzene saturation reactor 18 through a line 10 in mixture with a $C_5$ and $C_6$ paraffinic stream containing benzene which is charged through line 16. The resulting product is passed through line 20 to a separator 22 from which a hydrogen stream containing methane, water and hydrogen is recovered and passed through line 24 to hydrogen dryer 50 from which dried hydrogen containing methane is recovered through line 54 and passed to isomerization reactor 56. The reduced benzene paraffinic stream is recovered through line 32 and passed to feed dryer 36 and from feed dryer 36 through line 38 to line 54. Isomerization reactor 56 operates as discussed previously to produce an isomerized paraffinic stream with the hydrogen being optionally recycled to isomerization reactor 56, in part, or discharged from the process through line 62.

It has been discovered by the applicants that the benzene saturation reactor can tolerate substantial quantities i.e. up to at least about 100 ppmv of carbon monoxide, carbon dioxide or mixtures thereof in a hydrogen stream without inhibiting the benzene saturation catalyst to the extent that the benzene saturation reaction is adversely affected. It is preferred that the carbon oxide content be less than about 10.0 ppmv and desirably less than about 5.0 ppmv. While carbon oxides are known to temporarily poison and inhibit the functioning of benzene saturation catalysts it has been found that this damage is not significant when less than about 100 ppmv of carbon oxides are present in the hydrogen charged to benzene saturation reactor 18. In the practice of the process described above sufficient hydrogen is charged to benzene saturation reactor 18 so that hydrogen is available in sufficient quantities to flow in series through benzene saturation reactor 18 and isomerization reactor 56 to provide dried hydrogen from which carbon oxides have been removed for use in isomerization reactor 56 in the quantities required.

In the process of the present invention the requirement for methanation vessels for each process or at least one methanation vessel to supply hydrogen to the two processes has been eliminated. This is a significant process simplification leading to capital and operating cost savings. As noted previously, the benzene saturation catalyst can tolerate up to 100 parts ppmv of carbon oxides in a hydrogen stream without detriment to the benzene saturation reaction. These carbon oxides are methanated over the benzene saturation catalyst to produce methane and water. Any carbon oxides present in the $C_5/C_6$ paraffin stream are also methanated in the benzene saturation reactor. The water is subsequently removed in hydrogen dryer 50 and the methane is not detrimental to the isomerization reactions in isomerization reactor 56.

The paraffinic stream charged to benzene saturation reactor 18 and subsequently to isomerization reactor 56 comprises primarily $C_5/C_6$ paraffinic hydrocarbons. Hydrocarbons containing seven or more carbon atoms tend to crack in the isomerization reaction zone thereby producing undesirable carbon deposits on the catalyst and $C_4$ paraffins are generally isomerized in a separate process and used for other purposes. Benzene is saturated in the Benzene Saturation Reactor.

Figure 3:
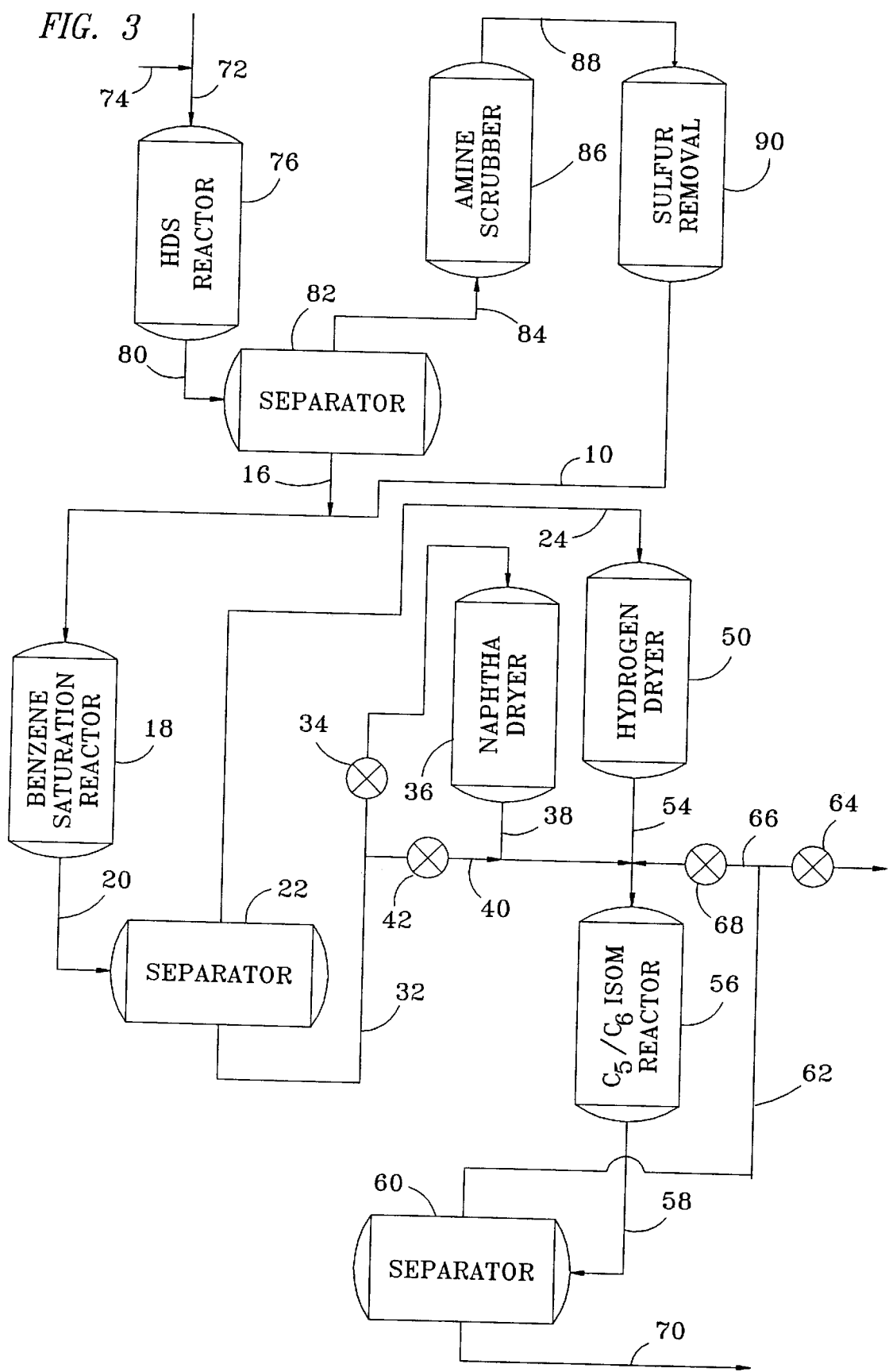
FIG. 3 is a schematic diagram of a further embodiment of the method of the present invention.

In FIG. 3 a variation of the process of the present invention is shown wherein a $C_5/C_6$ paraffinic feed stream which may contain carbon oxides is charged through a line 74 and combined with hydrogen that may contain carbon oxides supplied through a line 72 with the result that the combined stream may contain carbon oxides. The combined stream is passed via a line 80 to a hydrodesulfurization (HDS) reactor 76. Reactor 76 is a typical hydrodesulfurization reactor as known to those skilled in the art wherein sulfur compounds contained in a naphtha paraffinic stream are converted to hydrogen sulfide and recovered with the paraffinic stream through a line 80. The product stream is separated in a separator 82 into a paraffinic stream which is recovered via a line 16 and a hydrogen stream containing the hydrogen sulfide and carbon oxides which is passed via a line 84 to an amine, e.g. diethanolamine (DEA), scrubber 86 where hydrogen sulfide and some carbon dioxide are removed with the resulting hydrogen stream being passed through a line 88 to a second sulfur removal section 90 such as a zinc oxide sulfur absorber bed. The desulfurized hydrogen is then passed to benzene saturation reactor 18 through a line 10. The remaining portion of the process functions as described in the discussion of FIG. 2.

In many instances hydrogen available in refinery operations contains small amounts of carbon oxides. Such carbon oxides can be detrimental to the benzene saturation catalyst at high concentrations because of competitive adsorption. They are particularly detrimental and result in permanent deactivation of the isomerization reactor catalyst because of water produced from the methanation reaction. It is very desirable that such hydrogen streams be available for use in benzene saturation and in isomerization processes because sources free of carbon oxides are not always available. According to the present invention such streams are readily used in benzene saturation and isomerization processes with no detriment to either process. While the carbon oxides tend to temporarily deactivate the benzene saturation catalyst to a slight extent the deactivation is insufficient to inhibit the functioning of the catalyst for benzene saturation. Since the deactivation is temporary, the slight amount of deactivation caused by the presence of the carbon oxides in the hydrogen charged to the benzene saturation reactor does not result in sufficient cumulative detriment to the benzene saturation catalyst to prevent the effective saturation of benzene. The resulting hydrogen stream is then dried to remove the water and used in the isomerization reactor to isomerize the paraffin stream. The process of the present invention has thus resulted in the use of a hydrogen stream in parallel flow with the paraffin stream to remove undesirable carbon oxides at a point in the process where their removal is not detrimental to the function of the process to produce the clean carbon oxide-free hydrogen required for use in the isomerization reactor. The process of the present invention does not require a separate methanation reactor for either of or both the benzene saturation reactor and the isomerization reactor for carbon oxide removal. The paraffinic stream charged to the benzene saturation reactor will normally be reasonably dry but in the event that water beyond the tolerance level of the benzene saturation catalyst is present this stream may require drying. Such process requirements are well known to those skilled in the art.

Having thus described the present invention by reference to certain of its preferred embodiments it is pointed out that the embodiments described are illustrative rather than limiting in nature and that many variations and modifications are possible within the scope of the present invention. Such variations and modifications may be considered obvious and desirable by those skilled in the art based upon the foregoing description of preferred embodiments.

Having thus described the invention we claim:

1. A method for reducing the benzene content and isomerizing at least a portion of a paraffinic stream containing benzene and at least 50 volume percent $C_5$ and $C_6$ paraffins using a hydrogen stream containing at least one carbon oxide selected from the group consisting of carbon monoxide and carbon dioxide, the method comprising;

a) charging the paraffinic stream containing benzene and at least 50 volume percent $C_5$ and $C_6$ paraffins to a benzene saturation zone;

b) charging a hydrogen stream containing at least one carbon oxide to the benzene saturation zone;

c) saturating at least a major portion of the benzene and methanating at least a major portion of the carbon oxide present in the benzene saturation zone at a temperature from about 325° to about 800° F., a pressure from about 200 to about 700 psig in the presence of a benzene saturation catalyst to produce a reduced benzene content paraffinic stream and a reduced carbon oxide content hydrogen stream;

d) recovering the reduced benzene content paraffinic stream and the reduced carbon oxide content hydrogen stream;

e) drying at least a portion of the reduced carbon oxide content hydrogen stream to produce a dried reduced carbon oxide content hydrogen stream;

f) charging at least a portion of the dried reduced carbon oxide content hydrogen stream to an isomerization zone;

g) charging at least a portion of the reduced benzene content paraffinic stream to the isomerization zone; and, h) isomerizing at least a portion of the reduced benzene content paraffinic stream in the isomerization zone at a temperature from about 250° to about 600° F., and a pressure from about 100 to about 600 psig in the presence of an isomerization catalyst to produce an isomerized paraffin stream.

2. The method of claim 1 wherein the hydrogen stream contains more than about 5.0 ppmv of at least one carbon oxide.

3. The method of claim 1 wherein the hydrogen stream contains more than about 10.0 ppmv of at least one carbon oxide.

4. The method of claim 1 wherein the hydrogen stream contains from about 5.0 to about 100.0 ppmv of at least one carbon oxide.

5. The method of claim 1 wherein the benzene saturation catalyst comprises from about 0.1 to about 1.0 weight percent platinum supported on alumina.

6. The method of claim 1 wherein the average liquid hourly space velocity of the paraffin stream in the benzene saturation zone is from about 2 to about 10.

7. The method of claim 1 wherein the reduced carbon oxide content hydrogen stream contains less than about 0.1 ppmv carbon oxide.

8. The method of claim 1 wherein the isomerization catalyst comprises an acidic catalyst comprising from about 0.1 to about 2.0 weight percent platinum group metal component supported on a suitable support and up to about 20 weight percent acidic chloride components and wherein the isomerization zone is at a temperature from about 250° to about 600° F. and a pressure from about 100 to about 600 psig.

9. The method of claim 8 wherein the liquid hourly space velocity of the reduced benzene content paraffinic stream in the isomerization reactor is from about 1 to about 4.

10. The method of claim 1 wherein the paraffinic stream comprises a stream which has been desulfurized.

11. The method of claim 1 wherein the hydrogen stream has been desulfurized.

12. The method of claim 1 wherein at least a portion of the reduced benzene content paraffinic stream is dried prior to charging to the isomerization zone.

13. The method of claim 1 wherein the hydrogen is present in the isomerization zone in an amount equal to from about 500 to about 4000 standard cubic feet per barrel of reduced benzene content paraffinic stream.

* * * * *